(12) United States Patent
Lee et al.

(10) Patent No.: US 11,766,410 B2
(45) Date of Patent: Sep. 26, 2023

(54) COMPOSITION FOR PREVENTING OR TREATING DRY EYE SYNDROME CONTAINING α-HUMULENE AS ACTIVE INGREDIENT

(71) Applicant: INJE UNIVERSITY INDUSTRY-ACADEMIC COOPERATION FOUNDATION, Gimhae-si (KR)

(72) Inventors: Hyo-Jong Lee, Busan (KR); Su Jung Hwang, Gimhae-si (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 209 days.

(21) Appl. No.: 16/963,843

(22) PCT Filed: Dec. 28, 2018

(86) PCT No.: PCT/KR2018/016912
§ 371 (c)(1),
(2) Date: Jul. 22, 2020

(87) PCT Pub. No.: WO2019/151659
PCT Pub. Date: Aug. 8, 2019

(65) Prior Publication Data
US 2021/0038533 A1    Feb. 11, 2021

(30) Foreign Application Priority Data
Jan. 31, 2018  (KR) .......................... 10-2018-0012091

(51) Int. Cl.
*A61K 31/015* (2006.01)
*A23L 33/10* (2016.01)
*A61P 27/02* (2006.01)

(52) U.S. Cl.
CPC ............ *A61K 31/015* (2013.01); *A23L 33/10* (2016.08); *A61P 27/02* (2018.01); *A23V 2002/00* (2013.01); *A23V 2200/30* (2013.01)

(58) Field of Classification Search
CPC ..... A23L 33/10; A23L 33/105; A61K 31/015; A61P 27/02
See application file for complete search history.

(56) References Cited

U.S. PATENT DOCUMENTS

| | | | |
|---|---|---|---|
| 9,549,906 B2 | 1/2017 | Lynch et al. | |
| 2010/0130448 A1 | 5/2010 | Choi et al. | |
| 2015/0258040 A1* | 9/2015 | Lynch | ..................... A61P 25/02 |
| | | | 514/719 |
| 2018/0243236 A1* | 8/2018 | Hart | ........................ A23L 33/30 |

FOREIGN PATENT DOCUMENTS

| | | |
|---|---|---|
| JP | 07-215846 A | 8/1995 |
| KR | 10-2006-0043942 A | 5/2006 |
| KR | 10-2008-0107542 A | 12/2008 |
| WO | 2006-037194 A1 | 4/2006 |

OTHER PUBLICATIONS

International Search Report for PCT/KR2018/016912 dated May 10, 2019 from Korean Intellectual Property Office.
Rogero, A. P. et al., "Preventive and therapeutic anti-inflammatory properties of the sesquiterpene a-humulene in experimental airways allergic inflammation", British Journal of Pharmacology. 2009, vol. 158, pp. 1074-1087.
61st International Congress and Annual Meeting of the Society for Medicinal Plant and Natural Product Research, Sep. 1-5, 2013, Munster, Germany, pp. 1140-1142.
Marivane Lemos et al., "*Copaifera langsdorffii*: evaluation of potential gastroprotective of extract and isolated compounds obtained from leaves", Revista Brasileira de Farmacognosia 25, 2015, pp. 238-245.

* cited by examiner

*Primary Examiner* — Kara R McMillian
(74) *Attorney, Agent, or Firm* — Revolution IP, PLLC

(57) ABSTRACT

The present invention relates to a pharmaceutical composition for preventing or treating dry eye syndrome and a health functional food composition for preventing or improving dry eye syndrome including α-humulene as an active ingredient, wherein the α-humulene improves the expression level of mucin and recovers the reduced amount of tears in the dry eye-induced eye and thus can effectively prevent, improve or treat dry eye syndrome.

5 Claims, 2 Drawing Sheets
Specification includes a Sequence Listing.

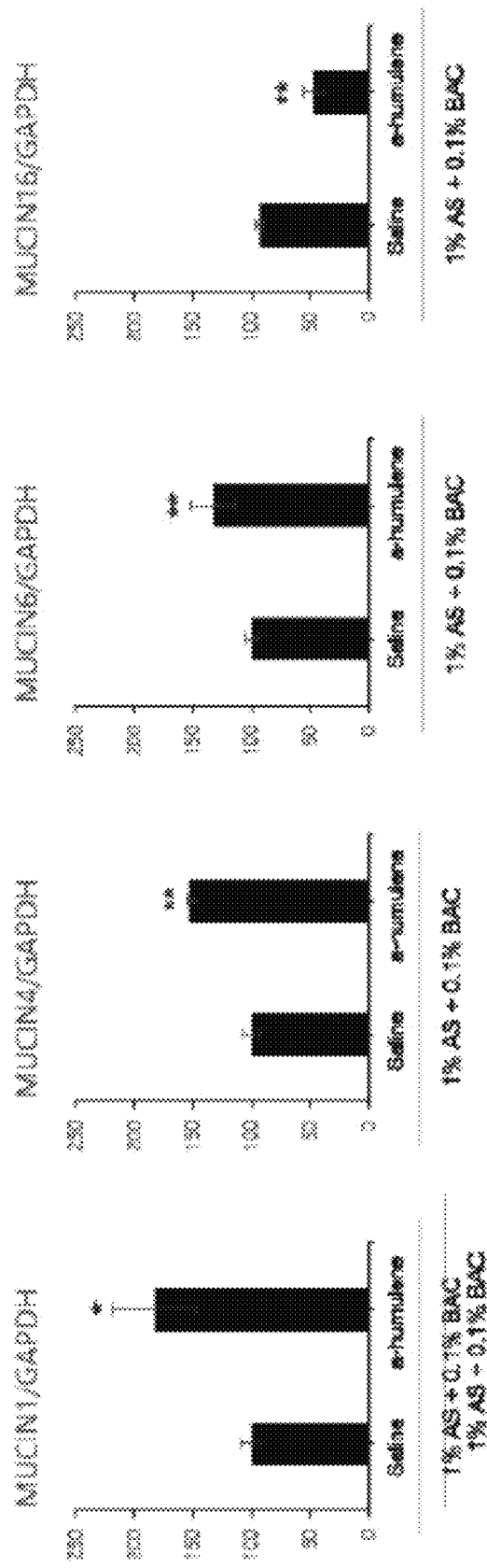
[FIG. 1]

[FIG. 2]
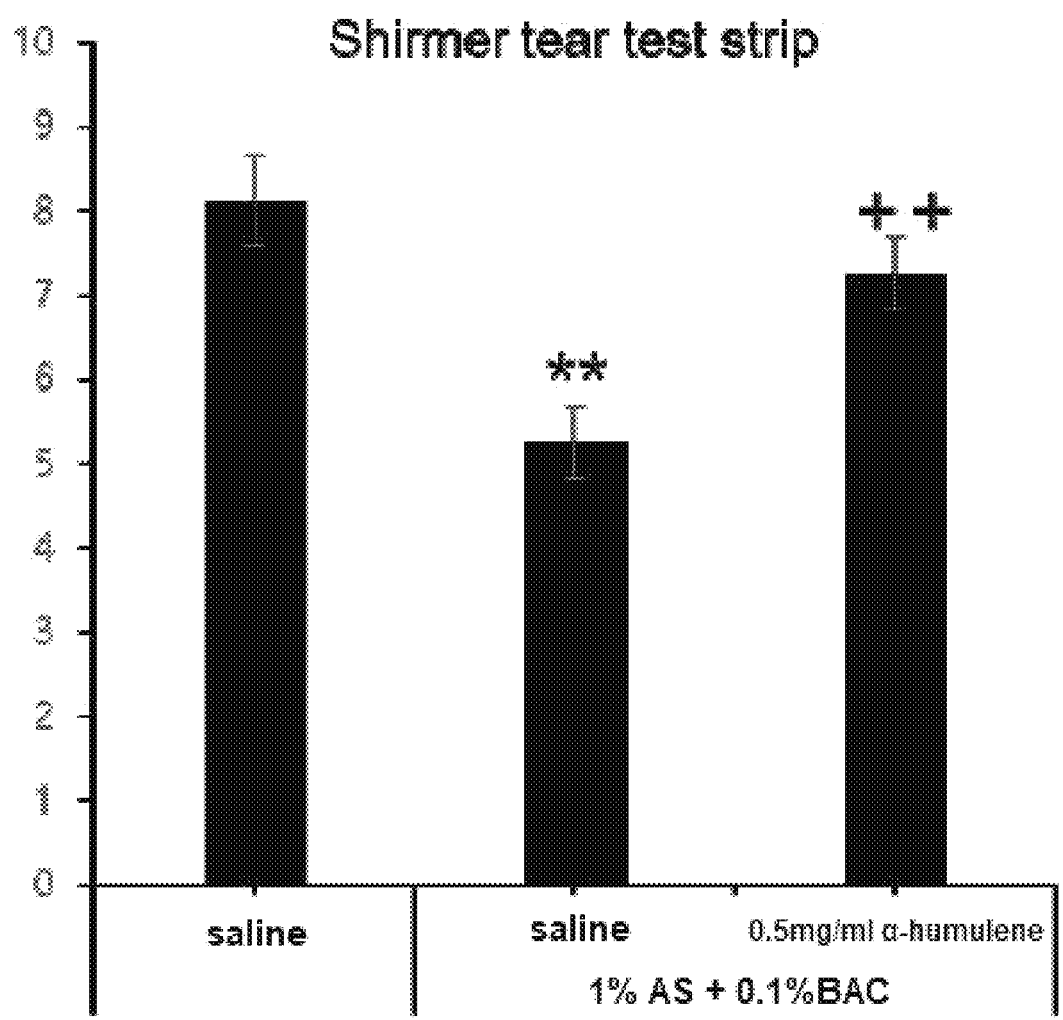

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgtacagtgg cacccattc                    20

<210> SEQ ID NO 2
<211> LENGTH: 20
<212> TYPE: DNA
<213> ORGANISM: Artificial Sequence
<220> FEATURE:

```
<223> OTHER INFORMATION: primer

<400> SEQUENCE: 2
gagtgtcatt gcggactgga                                                    20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gcttggacat ttggtgatcc                                                    20

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
gcccgttgag gtgtatttg                                                     19

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
tcctacttgc caggtcttcc aac                                                23

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
ttgtgggtgt tgacttcggt atag                                               24

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
aggcagcagt gcaggttatt                                                    20

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
tgaagcagga gacattgtaa acc                                                23
```

COMPOSITION FOR PREVENTING OR TREATING DRY EYE SYNDROME CONTAINING α-HUMULENE AS ACTIVE INGREDIENT

CROSS REFERENCE TO PRIOR APPLICATIONS

This application is a National Stage Application of PCT International Patent Application No. PCT/KR2018/016912 filed on Dec. 28, 2018, under 35 U.S.C. § 371, which claims priority to Korean Patent Application No. 10-2018-0012091 filed on Jan. 31, 2018, which are all hereby incorporated by reference in their entirety.

TECHNICAL FIELD

The present invention relates to a pharmaceutical composition or a health functional food composition for preventing or treating dry eye syndrome, which comprises alpha-humulene as an active ingredient.

BACKGROUND ART

Dry eye syndrome is a disease in which the incidence increases with age, 6% of the 40-year-old population suffers from dry eye disease, and the incidence rate increases to 15% with age and up to 25% of the 65 years and older population reported to suffer from dry eye syndrome.

Dry eye syndrome is a disease that is accompanied by damaged eye surface and symptoms such as irritation of the eyes such as foreign body sensation, dryness and decreased vision acuity due to lack of tears or excessive evaporation of tears, resulting in unbalance of tear components. The dry eye syndrome affects the quality of life by reducing functional vision and making it difficult to perform everyday tasks such as driving, reading and watching television.

In most cases of dry eye syndrome, an abnormality occurs in one of the oil layer, the water layer, or the mucous layer, which is a layer that complements the tear film, thereby causing corneal/conjunctival disorder. Among them, the abnormality of the mucosal layer causes serious corneal disorders. Dry eye syndrome increases the fluorescein permeability of corneal epithelial cells, conjunctival transformation and loss of goblet cells, causing pathological changes in epithelial cells on the corneal surface and thus it can cause corneal epithelial disorders or corneal epithelial sores, as well as corneal ulcers and eye infections. In some cases, corneal transplantation may be necessary.

Currently, the most widely used treatment for dry eye syndrome is a topical prescription of artificial tears containing viscoelastic compounds such as methylcellulose, chondroitin sulfate, and hyaluronic acid as a substitute for mucin, but since these compounds are physically and physiologically different from mucin, the efficacy of treatment is limited.

Meanwhile, α-humulene is a volatile organic compound of biological origin and is often found in many aromatic plants together with the isomeric form β-caryophyllene. It is known that β-caryophyllene has anti-cancer activity and anti-inflammatory activity. In addition, a past study reported that the essential oil component containing α-humulene showed anti-allergic activity in carrageenan-induced fore-limb-edema in mice by reducing the amount of TNF-α.

However, there has been no research on the effect of α-humulene for preventing, improving or treating dry eye syndrome.

DISCLOSURE

Technical Problem

An object of the present invention is to provide a pharmaceutical composition capable of preventing or treating dry eye syndrome caused by a decrease in mucin by increasing the expression of mucin.

Another object of the present invention is to provide a health functional food composition capable of preventing or improving dry eye syndrome caused by a decrease in mucin by increasing the expression of mucin.

Technical Solution

In order to achieve the above object, the present invention provides a pharmaceutical composition for preventing or treating dry eye syndrome comprising α-humulene as an active ingredient.

In order to achieve the other object, the present invention provides a health functional food composition for preventing or improving dry eye syndrome comprising α-humulene as an active ingredient.

Advantageous Effects

The present invention relates to a composition for preventing, improving or treating dry eye syndrome comprising α-humulene as an active ingredient, wherein the α-humulene improves the expression level of mucin and recovers the reduced amount of tears in rats with dry corneal damage and thus the composition can effectively prevent, improve or treat dry eye syndrome.

DESCRIPTION OF DRAWINGS

FIG. 1 shows a result of confirming the effect of improving the mucin expression of α-humulene according to an example of the present invention.

FIG. 2 shows a result of confirming the tear amount recovery effect of α-humulene according to the example of FIG. 1.

BEST MODE

Hereinafter, the present invention will be described in more detail.

The present invention provides a pharmaceutical composition for preventing or treating dry eye syndrome comprising α-humulene as an active ingredient.

The α-humulene may prevent or treat dry eye syndrome by increasing the expression of mucin in the eye. At this time, the mucin may be any one or more selected from the group consisting of MUC1, MUC4 and MUC6 and since the α-humulene exhibits an activity to increase the expression of mucin, dry eye syndrome may be more fundamentally treated.

In addition, the α-humulene can prevent or treat dry eye syndrome by restoring the amount of tears in the eye and thus this effect of restoring the amount of tears is shown by increasing the expression of mucin.

On the other hand, the α-humulene may be included in an amount of 0.1 to 50 parts by weight based on 100 parts by weight of the total composition and it is preferable that the mucin expression-enhancing activity of α-humulene is most effectively expressed within the range.

The pharmaceutical composition according to the present invention may further include a suitable carrier, excipient or diluent commonly used in the manufacture of pharmaceutical compositions in addition to the α-humulene. As a carrier, excipient or diluent usable in the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate, mineral oil and the like.

In one embodiment of the present invention, the pharmaceutical composition may be any one formulation selected from the group consisting of eye drops, granules, tablets, pills, capsules, gels, syrups, suspensions, emulsions, drops, liquids and injections, but it is not limited thereto.

In the case of formulation, it is prepared using diluents or excipients such as fillers, extenders, binders, wetting agents, disintegrating agents and surfactants. Solid preparations for oral administration include tablets, pills, powders, granules, capsules, etc. and these solid preparations may be prepared by mixing at least one excipient such as starch, calcium carbonate, sucrose, lactose or gelatin, etc.

In addition, lubricants such as magnesium stearate and talc are used in addition to simple excipients. Liquid preparations for oral administration may include suspensions, oral solutions, emulsions, syrups, etc. and may include various excipients such as wetting agents, sweetening agents, fragrances and preservatives in addition to water and liquid paraffin, which are commonly used simple diluents.

Formulations for parenteral administration include sterile aqueous solutions, non-aqueous solvents, suspensions, emulsions, freeze drying agents, suppositories. As the non-aqueous solvents and suspensions, propylene glycol, polyethylene glycol, vegetable oils such as olive oil, injectable esters such as ethyl oleate, and the like may be used. As the base of the suppository, witepsol, macrogol, tween 61, cacao butter, laurinum, glycerogelatin and the like may be used.

In addition, the dosage of the pharmaceutical composition according to the present invention can be increased or decreased depending on the route of administration, the degree of disease, sex, weight and age. Therefore, the above dosage does not limit the scope of the present invention in any way.

Moreover, the present invention provides a health functional food composition for preventing or improving dry eye syndrome comprising α-humulene as an active ingredient.

The α-humulene may prevent or improve dry eye syndrome by increasing the expression of mucin in the eye. At this time, the mucin may be any one or more selected from the group consisting of MUC1, MUC4 and MUC6 and since the α-humulene exhibits an activity to increase the expression of mucin, dry eye syndrome may be more fundamentally treated.

In addition, the α-humulene can prevent or improve dry eye syndrome by restoring the amount of tears in the eye and thus this effect of restoring the amount of tears is shown by increasing the expression of mucin.

The health functional food composition may contain various nutrients, vitamins, minerals (electrolytes), flavors such as synthetic flavors and natural flavors, etc., colorants and fillers (cheese, chocolate etc.), pectic acid and its salts, alginic acid and its salts, organic acids, protective colloid thickeners, pH adjusting agents, stabilizers, preservatives, glycerin, alcohols, carbonating agents used in carbonated drinks, and the like.

It may also contain flesh for the production of natural fruit juices, synthetic fruit juices and vegetable drinks. These components may be used independently or in combination. In addition, the health functional food composition may be in the form of any one of meat, sausage, bread, chocolate, candy, snack, confectionery, pizza, ramen, gum, ice cream, soup, beverage, tea, functional water, drink, alcohol and vitamin complex.

In addition, the health functional food composition may further include a food additive and compliance as a food additive is determined by the standards for the applicable item in accordance with General Regulations and General Test Methods of Korean Food Additives Codex approved by the Ministry of Food and Drug Safety, unless otherwise provided.

Examples of the items published in the above-mentioned "Korean Food Additives Codex" include chemical synthetics such as ketones, glycine, potassium citrate, nicotinic acid, and cinnamic acid and the like, natural additives such as persimmon color, licorice extract, crystalline cellulose, kaoliang color and guar gum and the like, mixed preparations such as L-sodiumglutamate preparation, alkaline agents for noodles, preservative formulation and a tar color formulation and the like.

Hereinafter, the present invention will be described in more detail through examples. These examples are only intended to illustrate the present invention in more detail, and it will be apparent to those skilled in the art that the scope of the present invention is not limited by these examples according to the gist of the present invention.

Preparation Example 1 Preparation of Reagents, Samples and Laboratory Animals

1. Preparation of Reagents

α-humulene, NaOH, methyl orange, calcium carbonate, hydrochloric acid and ethanol were purchased from Sigma-Aldrich (St. Louis, Mo., USA). Oligo (dT), dNTP, RNase-free water and Superscript III First-Strand Synthesis used in polymerase chain reaction (PCR) analysis were purchased from Invitrogen (Carlsbad, Calif., USA). The RNeasy mini kit and Rotor-Gene SYBR Green PCR Kit were purchased from Qiagen (Valencia, Calif., USA), and the oligonucleotide primer was purchased from Bioneer (Daejeon, Korea).

2. Experimental Animals

As a laboratory animal, a male Sprague Dawley white rat (Samtako, Korea) around 6 weeks of age was purchased and adjusted for 1 week in a constant temperature/humidity breeding device adjusted to a temperature of $23\pm1°$ C. and a humidity of $55\pm5\%$ (Daejong Instrument Industry Co., Ltd., Korea) for the experiment, and feed (Samtako, Korea) and drinking water were freely consumed during the entire experiment.

Example 1 Confirmation of Treatment Effect of α-Humulene for Dry Eye Syndrome

1. Experimental Method (1) Sample Administration Method

α-humulene was administered to the eye in the following way: 6 male rats with a body weight of about 200 g were used, and the left eye was designated as the control group and the right eye was designated as the experimental group. Samples as eye drops were administered to the eye twice a day for 5 days and 10 μl of physiological saline was administered to the left eye (control group) and 10 μl of 0.5 mg/ml α-humulene diluted in physiological saline was administered to the right eye (experimental group) as eye drops. Animals were sacrificed to extract the conjunctival epithelium containing the fornix conjunctiva from the eyes and the extracted tissue was isolated and used for molecular biological analysis.

(2) RNA Extraction and Gene Analysis

RNA was extracted from the ocular tissues of rats according to the manufacturers instructions using RNeasy mini kit from Qiagen (USA). The cDNA was synthesized using the cDNA synthesis kit of Qiagen (USA) from the isolated RNA, and then it was used for real-time polymerase chain reaction (real-time PCR). Real-time PCR was performed according to the manufacturer's instructions using Qiagen's Rotor-Gene Q 2 plex real-time DNA amplifier and Qiagen's two-step PCR SYBR kit, and the amount of amplified DNA was quantitatively compared. Specifically, after pre-denaturation at 95° C. for 5 minutes based on the cycling protocol, each 40 cycles were repeated at 95° C. for 5 seconds and at 60° C. for 10 seconds, and it was performed in the order of the melting step rising for 3 minutes from 60° C. to 95° C. The product amplified by the real-time PCR was quantified using the Delta delta Ct method, and corrected by the expression amount of β-actin for each sample. The base sequence of the primer used in the experiment was as shown in Table 1 below.

TABLE 1

| name | direction | Sequence (5' → 3') | SEQ ID |
|------|-----------|--------------------|--------|
| MUC1 | Forward | TGTACAGTGGCACCCCATTC | 1 |
|      | Reverse | GAGTGTCATTGCGGACTGGA | 2 |
| MUC4 | Forward | GCTTGGACATTTGGTGATCC | 3 |
|      | Reverse | GCCCGTTGAGGTGTATTTG | 4 |
| MUC6 | Forward | TCCTACTTGCCAGGTCTTCCAAC | 5 |
|      | Reverse | TTGTGGGTGTTGACTTCGGTATAG | 6 |

TABLE 1-continued

| name | direction | Sequence (5' → 3') | SEQ ID |
|------|-----------|--------------------|--------|
| MUC16 | Forward | AGGCAGCAGTGCAGGTTATT | 7 |
|       | Reverse | TGAAGCAGGAGACATTGTAAACC | 8 |

(3) Confirmation of Inhibition and Treatment Effect of Dry Corneal Epithelial Damage For experiments on dry corneal epithelial damage, an animal model of dry eye was prepared. It was induced by instill 1% atropine sulfate and 0.1% benzalkonium chloride twice a day for 2 weeks. After administration of the dry eye inducer, the experimental animals were applied by ocular administration according to the above-described administration method at an interval of 1 hour.

After administration of the sample for 2 weeks, the animals were anesthetized with isoflurane, and then the tear amount of each rat was measured using a Shrimer tear test strip.

2. Experimental Results

As a result, as shown in FIG. 1, when α-humulene was administered as an eye drop, it was confirmed that the expressions of representative biomarkers MUC1, MUC4 and MUC6 related to the tear film protection of the eye increased significantly.

In addition, as shown in FIG. 2, when the treatment with atropine sulfate/benzalkonium chloride (AS/BAC) reduced the amount of tears to induce dry eye, but it was confirmed that administration of 10 μl of 0.5 mg/ml α-humulene as an eye drop solution showed the therapeutic effect of the corneal epithelium. The reason for the significant difference in the amount of tears is that the amount of mucin increased with α-humulene treatment.

Accordingly, α-humulene exhibits an activity of increasing mucin expression related to the tear film protection of the eye, and thus can be used as a composition for preventing, improving symptoms and treating dry eye syndrome.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A method of increasing expression of mucin in an eye of a subject, comprising:
   providing a pharmaceutical composition comprising α-humulene as an active ingredient; and
   administering the pharmaceutical composition to the subject having a non-inflammatory dry corneal epithelial damage,
   wherein the mucin is at least one selected from the group consisting of MUC1, MUC4 and MUC6,
   wherein the α-humulene increases the expression of mucin in the eye so that dry eye syndrome is treated and an amount of tears in the eye is restored.

2. The method of claim 1, wherein the pharmaceutical composition is any one formulation selected from the group consisting of eye drops, granules, tablets, pills, capsules, gels, syrups, suspensions, emulsions, drops, liquids and injections.

3. A method of increasing expression of mucin in an eye of a subject, comprising:
   providing a health functional food composition comprising α-humulene as an active ingredient; and
   administering the health functional food to the subject having a non-inflammatory dry corneal epithelial damage,
   wherein the mucin is at least one selected from the group consisting of MUC1, MUC4 and MUC6,
   wherein the α-humulene increases the expression of mucin in the eye so that dry eye syndrome is improved and an amount of tears in the eye is restored.

4. The method of claim 1, wherein the α-humulene having an amount of 0.5 mg/ml is included in the pharmaceutical composition.

5. The method of claim 3, wherein the α-humulene having an amount of 0.5 mg/ml is included in the pharmaceutical composition.

* * * * *